United States Patent [19]
Pelle et al.

[11] Patent Number: 5,811,083
[45] Date of Patent: Sep. 22, 1998

[54] TOCOPHEROL DERIVATIVES FOR USE IN COSMETIC COMPOSITIONS

[75] Inventors: Edward Pelle, Valley Stream; Daniel H. Maes, Huntington, both of N.Y.

[73] Assignee: Estee Lauder, Inc., New York, N.Y.

[21] Appl. No.: 622,730

[22] Filed: Mar. 26, 1996

[51] Int. Cl.$^6$ .......................... A61K 7/40; A61K 31/355; C07D 311/04
[52] U.S. Cl. ............................ 424/59; 514/456; 514/458; 514/844; 514/847; 549/408; 549/405; 549/399
[58] Field of Search ..................................... 514/458, 456, 514/844, 847; 549/408, 405, 399; 424/59

[56] References Cited

U.S. PATENT DOCUMENTS

| | | | |
|---|---|---|---|
| 4,847,267 | 7/1989 | Deckner | 514/311 |
| 4,945,094 | 7/1990 | Salim | 514/264 |

FOREIGN PATENT DOCUMENTS

| | | |
|---|---|---|
| 0 471 584 A1 | 2/1992 | European Pat. Off. . |
| WO94/17096 | 8/1994 | WIPO . |

OTHER PUBLICATIONS

Ester M. Drug & Cosmetic Industry, p. 38, Sep. 1992.
Cort et al., "Antioxidant Activity and Stability of 6-Hydroxy-2,5,7,8-Tetramethylchroman-2-Carboxylic Acid", J. Amer. Oil Chem. Soc., 52:174–178, Jun. 1975.
Cort et al., "Proposed Antioxidant Exhibits Useful Properties", Food Technology, pp.46–50, Nov. 1975.
Taylor et al., "Antioxidant Activity of Amino Acids Bound to Trolox–C®", JAOCS, 622–626, May 1981.
Chemical Abstract, Registry No. 124382–56–5, 1985.
Pelle et al., "An In Vitro Model to Test Relative Antioxidant Potential: Ultraviolet–Induced Lipid Peroxidation in Liposomes", Archives of Biochem. and Biophys., 283(2):234–240, 1990.

*Primary Examiner*—Evelyn Huang
*Attorney, Agent, or Firm*—Pennie & Edmonds LLP

[57] ABSTRACT

Novel tocopherol derivatives useful for regulating skin aging and other skin disorders, as well as compositions containing the derivatives and methods for their use are described. The tocopherol derivative is tocopherol-cysteamine. Such types of skin atrophy to be treated the thinning of the epidermis and/or general degradation of the dermis often characterized by hyperplasia and structural disorganization. Such skin maladies include but are not limited to dry skin, severe dry skin, terosis, dandruff, keratoses, psoriasis, eczema, pruritus, age spots, lentigines, melasmas, wrinkles, blemished skin, hyperpigmented skin, hyperkeratotic skin, inflammatory dermatoses and age-related skin changes.

28 Claims, No Drawings

TOCOPHEROL DERIVATIVES FOR USE IN COSMETIC COMPOSITIONS

FIELD OF THE INVENTION

This invention relates to novel tocopherolderivatives useful for regulating skin aging and other skinmaladies, to pharmaceutical or cosmetic compositionscontaining such tocopherol derivatives and to methods fortheir use.

BACKGROUND OF THE INVENTION

The free radical theory of aging is one of the most widely accepted theories to explain the causes of aging. According to the free radical theory of aging, free radicals formed under aerobic conditions react with cellular components leading to cell damage and dysfunction and ultimately to what comprises the spectrum of accelerated aging. The cellular aspects of free radical damage have been studied by many and are well documented.

At the macroscopic level, the consequences of free radical damage are numerous. For example, in skin, free radical damage leads to alteration and degeneration of elastin and collagen in the dermis. In epidermis, markers of degeneration include lipofuscin granules and loss of rete pegs. These phenomena are directly related to the appearance of visible signs of cutaneous aging which include both chronologic aging and photoaging.

A major target of free radical damage is the cellular membrane and the extracellular matrix, which both contain abundant unsaturated lipids. When exposed to ultraviolet radiation, an environmental source of free radical generation in the skin, these unsaturated lipids may be transformed into lipid radicals via a bond-dissociating reaction and then undergo lipid peroxidation.

To counteract the destructive effects of free radicals, aerobic organisms have developed an array of enzymatic and nonenzymatic antioxidant defense mechanisms, including the antioxidant defense enzymes superoxide dismutase and catalase, and the low molecular mass free radical scavengers α-tocopherol (vitamin E) and reduced glutathione, all of which are present in the skin. Yet the extent of damage caused by free radicals seems to increase with age due to increased free radical production and/or a decrease in the ability of the antioxidant system to deal with these changes. Presently, exogenous natural and/or synthetic antioxidants are applied to the skin to supplement the endogenous antioxidant defense mechanism and thereby reduce or prevent damage caused by free radicals. 6-hydroxy-2,5,7,8-tetra-methylchroman-2-carboxylic acid (Trolox-C) is a lower homolog of atocopherol which has been found to have substantial antioxidant activity. W. M. Cort et al., *Food Tech.* 29(11):46 (1975); W. M. Cort et al., *JAOCS,*52:174 (1975). Trolox-C differs from α-tocopherol by having a carboxyl group in place of the isoprenoid side-chain of the αtocopherol. The phenolic hydroxyl group of Trolox-C is believed to be a free radical scavenger or antioxidant and has been shown to be an extremely effective antioxidant in both vegetable oils and animal fats. W. M. Cort et al., *Food Tech.* 29(11):46 (1975); W. M. Cort et al., *JAOCS,* 52:174 (1975). Trolox-C is relatively nontoxic and in Schaal thin layer oven and active oxygen method (AOM) tests, Trolox-C had greater antioxidant activity than α-tocopherol and other commercial food antioxidants such as butylated hydroxytoluene and butylated hydroxyanisole. W. M. Cort et al., *Food Tech.,* 29(11):46 (1975); W. M. Cort et al., *JAOCS,* 52:174 (1975).

Troloxyl-amino acids formed by an amide bond between the free carboxyl group of Trolox-C and the free amino group of the amino acid of various amino acids, such as cysteine, with potential antioxidant activity to Trolox-C, have been found to demonstrate greater antioxidant effectiveness than that of Trolox-C alone. Taylor et al., *JAOCS*p 624, (1985).

α-Tocopherol (vitamin E) having the formula:

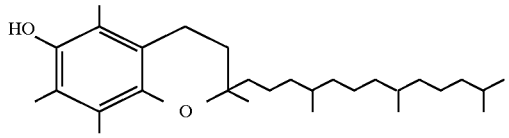

is a low molecular mass free radical scavenger within biological membranes. Reactive radicals such as OH can attack and damage membranes by setting off a free radical chain reaction known as lipid peroxidation. α-tocopherol inhibits this sequence by scavenging peroxy radical intermediates in the chain reaction.

One of the drawbacks associated with the use of α-tocopherol as an antioxidant that will retard lipid oxidation is that α-tocopherol has been shown to lose its antioxidant potency, and in fact become a pro-oxidant when stored at ambient temperatures over a period of one week. Pelle et al., *Archives of Biochemistry and Biophysic,* 283 (2), 234–240 (1990).

Thus, there is a need for a composition with the antioxidant properties of a-tocopherol but that does not have the α-tocopherol disadvantages. Generally, there is need for compounds having potent antioxidant properties greater than that of α-tocopherol and the stability such that it does not lose significant antioxidant activity over time.

The present invention provides novel tocopherol compounds with enhanced antioxidant activity.

The present invention also provides compounds which have the advantages of α-tocopherol with improved or greater stability.

The present invention provides novel compositions for regulating skin aging which comprise tocopherol-cysteamine.

Finally, the present invention also provides novel methods of regulating skin aging using compositions comprising tocopherol-cysteamine.

SUMMARY OF THE INVENTION

The present invention encompasses novel tocopherol derivatives useful in regulating skin aging and other skin maladies, compositions comprising these novel tocopherol derivatives and methods for the use of such novel tocopherol derivatives.

In particular, the present invention encompasses tocopherol-cysteamine. Tocopherol-cysteamine is a thio-derivative of tocopherol which has cysteamine bound by an amide linkage to the chromane ring of tocopherol. The cysteamine moiety is present in place of the normal phytl side chain found in α-tocopherol.

Thus the invention comprises tocopherol derivatives and pharmaceutically or cosmetically acceptable salts thereof, having the formula:

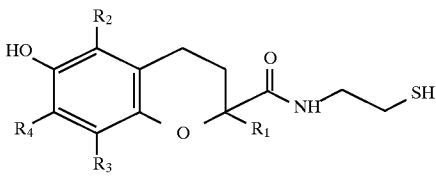

wherein $R_1$, $R_2$, $R_3$ and $R_4$ may be the same or different, and are independently selected from hydrogen, $C_1$ to $C_{18}$ alkyl group, substituted $C_1$ to $C_{18}$ alkyl group, $C_1$ to $C_{18}$ alkoxy group, substituted $C_1$ to $C_{18}$ alkoxy group, $C_1$ to $C_{18}$ alkenyl group, substituted $C_1$ to $C_{18}$ alkenyl group, $C_1$ to $C_{18}$ alkynyl group, substituted $C_1$ to $C_{18}$ alkynyl group. The $C_1$–$C_{18}$ alkyl, alkoxy, alkenyl or alkynyl groups may be straight chained e.g., n-propyl, n-butyl, n-pentyl or branch chained, e.g., iso-propyl, tert-butyl etc. Moreover, the above groups may be substituted by halogen, OH, SH, $NH_2$, $NO_2$ an the like.

Preferred compounds of this invention are obtained wherein $R_1$, $R_2$, $R_3$ and $R_4$ are lower unsubstituted alkyl groups. Lower alkyl being $C_1$ to $C_4$. Most preferred compounds are obtained wherein $R_1$, $R_2$, $R_3$ and $R_4$ are methyl.

In another embodiment of the invention $R_1$ is methyl and $R_2$, $R_3$, $R_4$ are the same or different and may be H; OH; lower alkyl; lower alkoxy; Cl; Br; F; $NO_2$; $NH_2$; $N(R_5)_2$, wherein $R_5$ is lower alkyl.

In further embodiments the invention encompasses cosmetic or pharmaceutical compositions comprising one or more compounds of formula II, or a pharmaceutically or cosmetically acceptable salt thereof, and a pharmaceutically or cosmetically acceptable carrier or excipient.

In a still further embodiment, the invention encompasses methods for regulating skin aging, including age-related skin changes comprising administering to a subject a safe and effective amount of a composition comprising one or more compounds of formula II, or a pharmaceutically or cosmetically acceptable salt thereof and a pharmaceutically or cosmetically acceptable carrier or excipient. A preferred method of administering the compositions of the present invention is by topical administration.

In yet another embodiment, the invention encompasses methods for treating disorders including but not limited to dry skin, severe dry skin, terosis, dandruff, keratoses, psoriasis, eczema, erythema (due to sunburn, chemical drug allergies, etc.), age spots, lentigines, melasmas, wrinkles, (both coarse and fine, caused intrinsic as well as extrinsic damage), blemished skin, hyperpigmented skin, hyperkeratotic skin, and inflammatory dermatoses. The invention also encompasses the use of the novel antioxidants in sunscreen compositions having a sunscreen agent and a carrier. The novel antioxidants are useful in such compositions to protect the skin from the harmful extrinsic affects the UV-light has on the skin.

The compounds of the present invention surprisingly demonstrate a stability and pharmaceutical activity or cosmetic effects against lipid oxidation not previously achieved by α-tocopherol itself or by the combination of α-tocopherol and other antioxidants.

The present invention may be understood more fully by reference to the detailed description and illustrative examples which are intended to exemplify non-limiting embodiments of the invention.

DETAILED DESCRIPTION OF THE INVENTION

Definitions

As used herein, "skin aging" includes skin atrophy and means the thinning and/or general degradation of the dermis caused by free radical damage which is often characterized by an alteration and degeneration of collagen and/or elastin. In epidermis, markers of degeneration include lipofuscin granules and loss of rete pegs. Skin aging may be caused by either intrinsic or extrinsic factors such as natural chronoaging, photodamage, burns, or chemical damage.

As used herein, "regulating skin aging" means preventing, retarding, arresting, treating, or reversing the process of skin aging in mammalian skin.

As used herein "tocopherol derivative" means a tocopherol-cysteamine of the structure:

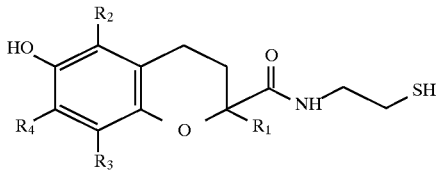

or pharmaceutically or cosmetically acceptable salts thereof, wherein $R_1$, $R_2$, $R_3$ and $R_4$ may be the same or different, and are independently selected from hydrogen, $C_1$ to $C_{18}$ straight or branch chained alkyl groups, substituted $C_1$ to $C_{18}$ is alkyl groups, $C_1$ to $C_{18}$ is alkoxy groups, substituted $C_1$ to $C_{18}$ is alkoxy groups, $C_1$ to $C_{18}$ is alkenyl groups, substituted $C_1$ to $C_{18}$ is alkenyl groups, $C_1$ to $C_{18}$ is alkynyl groups, substituted $C_1$ to $C_{18}$ is alkynyl groups. Those groups may be substituted by halogen, OH, SH, $NH_2$ $NO_2$ and pharmaceutically or cosmetically acceptable salts thereof. The compounds encompassed have antioxidant activity, improved stability in storage, and are suitable for formulations in cosmetics or pharmaceuticals.

As used herein, "alkyl" means a monovalent radical, such as ethyl, having the general formula $C_nH_{2n+1}$.

As used herein, "alkoxy" means an alkyl radical attached to the remainder of the molecule by oxygen, e.g., methoxy, ethoxy, butoxy, etc.

As used herein, "alkenyl" means an unsaturated, univalent aliphatic radical having the general formula $C_nH_{2n-1}$.

As used herein, "alkynyl" means an unsaturated hydrocarbon radical having the general formula $C_nH_{n-1}$ and containing a triple bond between two carbon atoms.

As used herein, "safe and effective amount" means an amount of compound or composition sufficient to significantly induce a positive modification of the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound, compounds or composition employed, the particular pharmaceutically-acceptable carrier utilized, and like factors within the knowledge and expertise of the attending physician or health care provider.

As used herein, "cosmetic" means articles intended to be applied to the human body or any part thereof for cleansing, beautifying, promoting attractiveness or altering the appearance thereof.

As used herein, "pharmaceutical" means articles intended for use in the diagnosis, cure, mitigation, treatment or prevention of disease or biological disorders in mammals, including humans.

Synthesis

The compounds of the present invention can be synthesized in accordance with standard organic chemical techniques using readily/commercially available starting materials. Examples of the synthesis of such compounds are described below in Scheme 1.

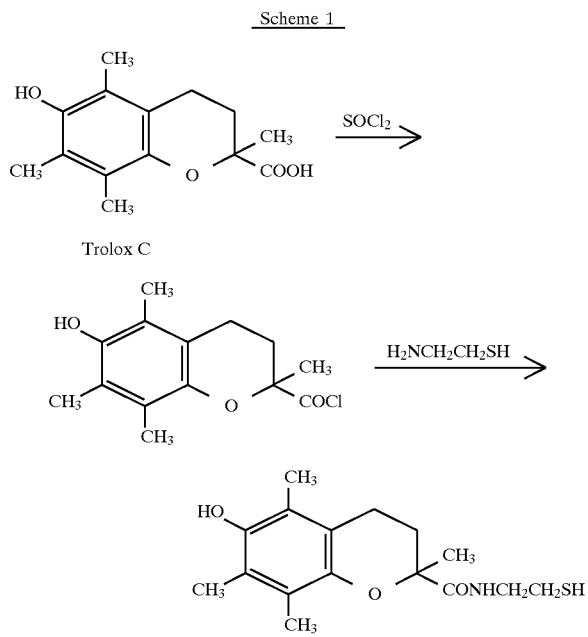

Compositions and Formulations Thereof

The compositions of the present invention can be used to regulate skin aging, and other disorders including but not limited to dry skin, dandruff, keratoses, psoriasis, eczema, erythema (due to sunburn, chemical drug allergies, etc.), age spots, lentigines, melasmas, wrinkles (both coarse and fine, caused by intrinsic as well as extrinsic damage), blemished skin, hyperpigmented skin, hyperkeratotic skin, inflammatory dermatoses and age-related skin changes.

In regulating skin aging or other skin disorders as described above, compositions containing about 0.001 to about 50.0 wt. %, preferably about 0.005 to about 10.0 wt. %, and most preferably 0.01 to about 1.0 wt. % of the tocopherol derivative can be employed.

It should be understood that two or more tocopherol derivatives of the present invention can be used in combination such that the combined weight % of those derivatives used in the above-mentioned compositions is within those ranges mentioned above.

Both pharmaceutical and cosmetic compositions are preferably to be applied topically, so as to minimize systemic effects or undesirable side effects. The novel compounds may also be employed in pharmaceutical compositions suitable for parenteral (including subcutaneous, transdermal, intramuscular and intravenous) administration, although the most suitable route in any case will depend on the nature and severity of the condition being treated. The most preferred mode of administration for treating skin disorders, in particular skin aging or the skin disorders described above, is topical. In addition, the novel compounds of the present invention may be further employed in cosmetic compositions. In such an instance, the preferred mode of administration for treating skin disorders, in particular skin aging, is topical.

The compounds of the present invention can be formulated into suitable cosmetic or pharmaceutical compositions depending on the particular use for which it is to be intended, for example, cosmetic or therapeutic, or both. The cosmetic compositions can comprise one or more of the derivatives of formula II and a pharmaceutically or dermatologically acceptable carrier or excipient.

The compositions of the present invention, useful for topical application, may contain additional ingredients such as carrier, excipient or vehicle ingredients such as, for example, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments which are non-toxic and pharmaceutically or dermatologically acceptable. Additionally, moisturizers or humectants can be added to the present compositions if desired. Examples of such additional ingredients can be found in *Remington's Pharmaceutical Sciences,* Eighteenth Edition, A. R. Gennaro, Ed., Mack Publishing Co., Easton, Pa., 1990 and *The International Cosmetic Ingredients Dictionary,* 4th Edition, The Cosmetic, Toiletry, and Fragrance Association, Inc., Washington D.C., 1991 CTFA.

In addition to these and other vehicles which will be obvious to those of ordinary skill in the art, it will be understood that the pharmaceutical or cosmetic compositions of the present invention may include other ingredients such as those that improve or eradicate age spots, keratoses and wrinkles; other ingredients include but are not limited to analgesics; anesthetics; antiacne agents; antibacterials; antiyeast agents; antifungal agents; antiviral agents; antidandruff agents; antidermatitis agents; antipruritic agents; antiemetics; antimotion sickness agents; antiinflammatory agents; antihyperkeratolytic agents; antidryskin agents; antiperspirants; antipsoriatic agents; antiseborrheic agents; hair conditioners and hair treatment agents; antiaging or anti-wrinkle agents; sunscreen agents; antihistamine agents; skin lightening agents; depigmenting agents; vitamins; corticosteroids; tanning agents; hormones; retinoids; clotrimazole; ketoconazole; miconazole; griseofulvin; hydroxyzine; diphenhydramine; pramoxine; lidocaine; procaine; mepivacaine; monobenzone; erythidocaine; procaine; mepivacaine; monobenzone; erythromycin; tetracycline; clindamycin; meclocyline; hydroquinone; minocycline; naproxen; ibuprofen; theophylline; cromolyn; albuterol; retinoic acid; 13-cis retinoic acid; hydrocortisone; hydrocortisone 21-acetate; hydro-cortisone 17-valerate; hydrocortisone 17-butyrate; betamethasone valerate; betamethasone dipropionate; triamcinolone acetonide; fluocinonide; clobetasol propionate; benzoyl peroxide; crotamiton; propranolol; promethazine; vitamin A palmitate; vitamin E acetate and mixtures thereof.

The compounds of the present invention can be used as their pharmaceutically or cosmetically acceptable salts. Such salts may be prepared from pharmaceutically acceptable non-toxic acids or bases including inorganic and organic acids or inorganic and organic bases. Such salts may contain any of the following anions: acetate, benzensulfonate, benzoate, camphorsulfonate, citrate, fumarate, gluconate, hydrobromide, hydrochloride, lactate, maleate, mandelate, mucate, nitrate, pamoate, phosphate, succinate, sulfate, tartrate and the like. Particularly preferred are benzensulfonate, hydrobromate, hydrochloride and sulfate. Such salts may also contain the following cations: aluminum, calcium, lithium, magnesium, potassium, sodium, zinc, benzathine, chloroprocaine, choline, diethanolamine, ethylenediamine, meglumine and procaine.

METHODS FOR REGULATING SKIN AGING AND OTHER DISORDERS

The present invention also relates to a method for regulating skin aging or other skin disorders including but not limited to dry skin, severe dry skin, terosis, dandruff, keratoses, psoriasis, eczema, age spots, lentigines, melasmas, wrinkles (both coarse and fine, caused by intrinsic as well as extrinsic damage), blemished skin, hyperpigmented skin, hyperkeratotic skin, inflammatory dermatoses and age-related skin changes. Such a method comprises administering or topically applying to the skin a safe and effective amount of one or more of the novel tocopherol derivatives of the present invention. While the present invention relates to novel tocopherol derivatives used to treat skin disorders, the present invention further relates to the use of compositions, such as those discussed above, comprising one or more of said tocopherol derivatives, to be used for treating skin disorders. The amount of tocopherol derivatives and frequency of treatment will vary widely depending upon the level of skin aging already in existence in the subject (if such exists), the rate of further aging, and the level of regulation desired.

A preferred method of pharmaceutically treating the skin is via chronic topical application of a safe and effective amount of the tocopherol derivative to regulate skin aging to treat other skin maladies described above. The amount of tocopherol derivative and frequency of topical application to the skin can vary widely, depending upon the particular skin disorder and the severity thereof. It is well within the purview of the skilled artisan, such as a dermatologist or other health care provider, to regulate pharmaceutical dosages according to patient needs.

It is suggested as an example that topical application range from about once per week to about 4 or 5 times daily, preferably from about 3 times a week to about 3 times daily, most preferably about once or twice per day. The composition for topical application will comprise from about 0.001 to about 50.0 wt. %, preferably about 0.005 to about 10.0 wt. % and most preferably 0.01 to about 1.0 wt. % of the tocopherol derivative or mixture of tocopherol derivatives.

By "chronic" application, it is meant herein that the period of topical application may be over the lifetime of the patient, preferably for a period of at least about one month, more preferably from about three months to about twenty years, more preferably from about six months to about ten years, more preferably still from about one year to about five years, thereby resulting in regulation of skin aging or other skin maladies described above.

A preferred method of cosmetically treating the skin is via occasional topical application of a safe and effective amount of the tocopherol derivative. Such cosmetic uses include but are not limited to moisturizing skin; masking skin blemishes or other undesired attributes; highlighting the skin as, for example, an eye shadow; improving skin texture; and the like. The amount of tocopherol derivative and frequency of topical application to the skin can vary widely, depending upon desirability of use. The composition for topical application will comprise from about 0.001 to about 50.0 wt. %, preferably about 0.005 to about 10.0 wt. % and most preferably 0.01 to about 1.0 wt. % of the tocopherol derivative or mixture of tocopherol derivatives.

In another embodiment of the invention, regulating skin aging or treating other skin maladies described above involves applying both a safe and effective amount of the tocopherol derivative(s) and a safe and effective amount of one or more of a sunscreening agent, an anti-inflammatory agent, a skin atrophy regulating agent, a chelating agent, an additional anti-oxidant/radical scavenging agent, a retinoid and/or a benzofuran derivative to the skin simultaneously.

As used herein, "simultaneous application" or "simultaneously" means applying the agents to the skin at the same site on the body at about the same time. Though this can be accomplished by applying the agents separately to the skin, preferably a composition comprising all the desired agents commingled is applied to the skin. The amount of sunscreening agent applied is generally from about 0.02 mg to about 1.0 mg per $cm^2$ skin. The amount of anti-inflammatory agent applied is generally from about 0.005 mg to about 0.5 mg, preferably from about 0.01 mg to about 0.1 mg per $cm^2$ skin. The amount of chelating agent generally applied is from about 0.001 mg to about 1.0 mg, preferably from about 0.01 mg to about 0.5 mg, more preferably from about 0.05 mg to about 0.1 mg per $cm^2$ skin. The amount of retinoid applied is generally from about 0.00001 mg to about 0.02 mg per $cm^2$ skin. The amount of benzofuran derivative applied is generally from about 0.001 mg to about 1.0 mg/$cm^2$ skin per application, preferably from about 0.01 to about 0.5 mg/$cm^2$ skin per application. The amount of steroid ester(s) applied is generally from about 0.001 mg to about 1.0 mg per $cm^2$ skin per application, preferably from about 0.01 mg to about 0.5 mg per $cm^2$, more preferably from about 0.05 to about 0.25 mg/$cm^2$ skin per application, which may vary upon the severity of the condition to be treated and the efficacy of the compounds employed.

Examples

The following examples demonstrate the unique and unexpected properties of the present invention.

However, the present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

Example No. 1

The antioxidant potential and stability of equimolar concentrations of tocopherol-cysteamine, cysteamine, and a α-tocopherol were compared using an in vitro liposomal/UV assay. This assay provides an effective means of measuring an antioxidant's potential to inhibit UV-induced lipid peroxidation which may correlate with the antioxidant's inhibition of free radical generation in the skin.

The antioxidant activity of tocopherol-cysteamine was determined to be greater than that activity observed in both the α-tocopherol and cysteamine assays combined. As illustrated in Table I, the inhibition of UV-induced lipid peroxidation by 0.18 mM tocopheroi-cysteamine was determined to be 67.3%. This percentage of lipid peroxidation is consistent with the findings of previous experiments in which triplicate samplings assayed in duplicate, had an average of 65.2% (+/−3.61) inhibition.

Table I also shows that at the same concentration, tocopherol was observed to inhibit lipid peroxidation by 28.9%. The antioxidant contribution of cysteamine to the derivative was tested by measuring cysteamine alone and determined to be 20.1%. These results indicate that the improved antioxidant activity of tocopherol-cysteamine over tocopherol is not due to an additive effect of cysteamine, which is also an antioxidant.

TABLE I

| Ingredient | Concentration | % Inhibition |
| --- | --- | --- |
| Tocopherol | 0.18 mM | 28.9% |
| Cysteamine | 0.18 mM | 20.1% |
| Tocopherol-cysteamine | 0.18 mM | 67.3% |

Furthermore, in addition to being a more potent antioxidant than α-tocopherol, tocopherol-cysteamine is considerably more stable. The tocopherol sample used in this assay was freshly prepared and stored under argon gas in a sealed amber ampoule at −20° C. These precautions were required because α-tocopherol has been shown to gradually lose antioxidant potency and become a prooxidant when stored at ambient temperatures over a period of 1 week. In contrast, the tocopherol-cysteamine samples used in the assay were stored in dry powder form at ambient temperatures for more than five years. The tocopherol-cysteamine did not lose significant antioxidant activity over this five year period.

Example No. 2

An experiment was performed which demonstrated that tocopheryl-cysteamine does not lose any significant antioxidant activity after storage for a five year period at ambient temperatures.

In particular, several materials, including two batches of tocopherol-cysteamine, were tested for anti-oxidant activity using a UV/liposomal assay. The results for the tocopherol-cysteamine compounds are reported below in Table II. The results reported below represent the average of two separate assays performed in duplicate.

TABLE II

| Ingredient | Concentration | Inhibition |
| --- | --- | --- |
| Tocopherol-cysteamine (new batch) | 0.010% | 65.6% |
| Tocopherol-cysteamine (5 year-old) | 0.010% | 57.3% |

As illustrated above, the activity of the 5 year-old tocopherol-cysteamine is very similar to that of the new batch of tocopherol-cysteamine.

Example No. 3

A clinical study was undertaken in order to measure the effectiveness of topically applied compositions containing tocopherol-cysteamine on human skin. Protection against lipid peroxidation was used as a biological marker in a study of twenty subjects.

A cream containing 0.10% tocopherol-cysteamine and other antioxidants was prepared using the batch formulation of Table III.

TABLE III

| Ingredient | % by Weight |
| --- | --- |
| Perfecta 239A | 3.000 |
| Promulgen D-CG | 1.500 |
| Cerasynt Q | 1.500 |
| Lipocol C/Cetyl Alcohol NF | 1.500 |
| Robane | 6.000 |
| Vitamin E Acetate | 2.000 |
| MYRJ 59 Flaked | 1.200 |
| BRIJ 76 | 0.800 |
| Dow Corning Q2-1403 Fluid | 2.500 |
| Super Sterol Ester | 1.500 |
| Naturechem CR | 1.500 |

TABLE III-continued

| Ingredient | % by Weight |
| --- | --- |
| Ceraphyl 424 | 1.500 |
| BHT (Food Grade) | 0.100 |
| Wickenol 171 | 1.000 |
| Hexylene Glycol | 1.000 |
| Stabex | 0.100 |
| Deionized Water | 48.499 |
| 1,3 Butylene Glycol | 2.000 |
| Nikkol VC-PMG | 1.000 |
| N-Acetyl-L-Cysteine USP | 0.500 |
| Methyl Paraben NF | 0.300 |
| Sequestrene NA3T/Sequestrene NA3 | 0.100 |
| Emeressence 1160 | 0.500 |
| Veegum HV (4M Dispersion) | 15.000 |
| 1,3 Butylene Glycol | 1.500 |
| Keltrol F | 0.200 |
| 1,3 Butylene Gylcol | 1.500 |
| Ubidecarenone/Ubiquinone 50 | 0.100 |
| Alcohol SDA 40-B 200 Proof | 0.500 |
| Tocopherol-cysteamine | 0.100 |
| Standapol ES-2 | 0.500 |
| Deionized Water | 1.000 |
| L-Selenomethionine | 0.001 |

The cream containing 0.10% tocopherol-cysteamine was applied by the panelists to their left ventral forearms twice daily. The same cream formulation without any antioxidants was used as the control and applied to the right ventral forearms. At 0, 4, 8 and 12 weeks, ethanol washes were taken and samples aliquoted for endogenous levels of lipid peroxides, susceptibility to lipid peroxidation by UVB irradiation at 500 mJ/cm$^2$, and lipid analysis.

The results from each time point are shown in Table IV below.

TABLE IV

| | Tocopherol-cysteamine | | Control Composition | |
| --- | --- | --- | --- | --- |
| Week | 0 + Ao | 500 mJ/cm$^2$ + Ao | 0 | 500 mJ/cm$^2$ |
| 0 | 9.10 | 17.69 | 11.11 | 17.886 |
| 4 | 8.19 | 12.95 | 12.75 | 18.04 |
| 8 | 6.56 | 10.33 | 11.44 | 15.69 |
| 12 | 21.19 | 26.67 | 24.33 | 31.44 |

As can be seen from these data, the average level of peroxides increases after irradiation but is inhibited in samples extracted from arms which received the tocopherol-cysteamine treatment regimen. Additionally, these levels decreased over the course of treatment. Further, in samples treated with tocopherol-cysteamine but not irradiated, the average endogenous peroxide levels also decreased over time. When the 0 time point of the tocopherol-cysteamine treated arm was compared to itself after 8 weeks of treatment there was a significant decrease (p<0.01, t test) in the amount of peroxides generated by UVB. There was also a significant decrease in amount of endogenous peroxides from the 0 time point to the 8 week time point at a p value less than 0.1.

As can be seen from the data in Table IV, at the 12 week time point, the average values of the tocopherol-cysteamine treated samples are lower than the untreated samples for both the control and irradiated preparations. This follows the same trend observed for the first eight weeks of treatment.

These results indicate that long term, topical application of tocopherol-cysteamine contributes to the reduction in the level of endogenous peroxides. They also demonstrate that treatment provides protection against UVB-induced lipid peroxidation and that susceptibility to oxidation can be minimized.

It may be apparent to those skilled in the art that modifications and variations of the present invention are possible in light of the above disclosure. It is understood that such modifications are within the spirit and scope of the invention, which is limited and defined only by the appended claims.

What is claimed is:

1. A compound having the structure:

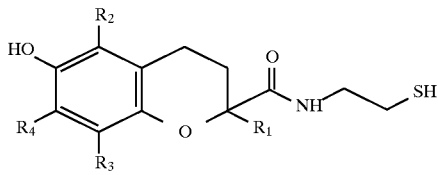

II wherein $R_1$, $R_2$, $R_3$ and $R_4$ are methyl; or a pharmacentically or cosmetically acceptable salt thereof.

2. A compound having the structure:

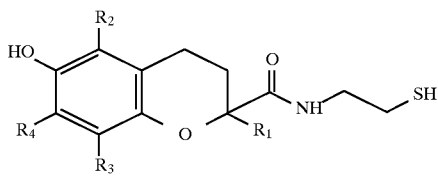

II or a pharmaceutically or cosmetically acceptable salt thereof, wherein $R_1$, $R_2$, $R_3$ and $R_4$ are the same or different, and are independently selected from the group consisting of hydrogen, $C_1$ to $C_{18}$ alkyl group, substituted $C_1$ to $C_{18}$ alkyl group $C_1$ to $C_{18}$ alkoxy group, substituted $C_1$ to $C_{18}$ alkixy group, $C_2$ to $C_{18}$ alkenyl group, substituted $C_1$ to $C_{18}$ alkynyl group, and substituted $C_2$ to $C_{18}$ alkynyl group; wherein said groups are optionally substituted with halogen, OH, SH, $NH_2$, or $NO_2$.

3. A composition for treating or retarding lipid peroxidation-mediated medicated skin aging or a lipid peroxidation-medicated skin disorder which comprises a lipid-peroxidation inhibiting amount of a compund having a structure:

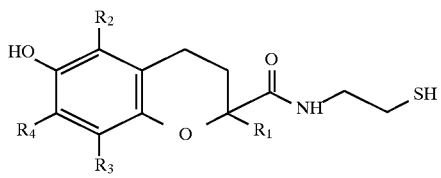

or a pharmaceutically or cosmetically acceptable salt thereof wherein $R_1$, $R_2$, $R_3$ and $R_4$ are the same or different, and are independently selected from the group consisting of hydrogen, $C_1$ to $C_{18}$ alkyl group, substituted $C_1$ to $C_{18}$ alkyl group, $C_1$ to $C_{18}$ alkoxy group, substituted $C_1$ to $C_{18}$ alkoxy group, $C_2$ to $C_{18}$ alkyeyl group substituted $C_2$ to $C_{18}$ alkenyl group $C_2$ to $C_{18}$ alkynyl group, and substituted $C_2$ to $C_{18}$ alkynyl group, and wherein the groups are optionally substituted with halogen, OH, SH, $NH_2$, or $NO_2$; and a carrier.

4. The composition of claim 3, comprising a compound wherein $R_1$, $R_2$, $R_3$ and $R_4$ are methyl.

5. The composition of claim 3 wherein said carrier is a pharmaceutically or cosmetically acceptable vehicle.

6. The composition of claim 3 wherein said compound is present in an amount of about 0.001 wt. % to about 50.0 wt. % of the composition.

7. The composition of claim 3 wherein said compound is present in an amount of about 0.005 wt. % to about 10.0 wt. % of the composition.

8. The composition of claim 5 wherein said vehicle is selected from the group consisting of lotion, tincture, cream, emulsion, gel and ointment.

9. The composition of claim 3 wherein said composition is a topical composition.

10. A method for treating or retarding lipid peroxidation-mediated skin aging or treating a lipid peroxidation-mediated skin disorder in a patient which comprises topically administering to skin of a patient in need thereof a composition comprising a lipid-peroxidation inhibiting amount of a compound formula:

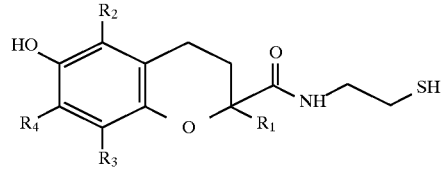

or a pharmaceutically or cosmetically acceptable salt thereof, wherein $R_1$, $R_2$, $R_3$ and $R_4$ are the same or different, and are independently selected from the group consisting of hydrogen, $C_1$ to $C_{18}$ straight or branch chained alkyl group, substituted $C_1$ to $C_{18}$ alkyl group, $C_1$ to $C_{18}$ alkoxy group, substituted $C_1$ to $C_{18}$ alkoxy group, $C_2$ to $C_{18}$ alkenyl group, substituted $C_2$ to $C_{18}$ alkenyl group, $C_2$ to $C_{18}$ alknyl group, and wherein the groups are optionally substituted with halogen, OH, SH, $NH_2$, or $NO_2$; and a carrier.

11. The method of claim 10, comprising a compound wherein $R_1$, $R_2$, $R_3$ and $R_4$ are methyl.

12. The method of claim 10, wherein said skin disorder is selected from the group consisting of dry skin, severe dry skin, terosis, dandruff, keratoses, psoriasis, czema, erythema age spots, lentigines, melasmas, wrinkles, blemished skin, hyperpigmented skin, hyperkeratotic skin, and inflammatory dermatoses.

13. The method of claim 10, wherein said compound is present in an amount of about 0.001 wt. % to about 50.0 wt. % of the composition.

14. The method of claim 10, wherein said compound is present in an amount of about 0.005 wt. % to about 10.0 wt. % of the composition.

15. The method of claim 10, wherein said carrier is selected from the group consisting of lotion, tincture, cream, emulsion, gel and ointments.

16. The method of claim 10 wherein said skin aging is age-related skin changes.

17. A composition for treating or retarding lipid peroxidation-medicated skin aging or a lipid peroxidation-medicated disorder which comprises a liquid peroxidation inhibiting amount of a compound having the structure:

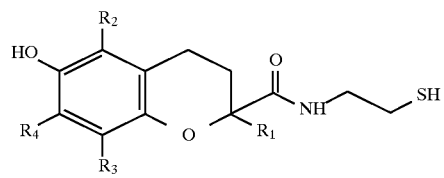

or a pharmaceutically acceptable salt thereof wherein $R_1$ is methyl and $R_2$, $R_3$, $R_4$ are the same or different and are independently selected from H, OH, lower alkyl, lower alkoxy, halogen, $NO_2$, $NH_2$ or $N(R_5)_2$, wherein $R_5$ is lower alkyl; and a carrier.

18. The composition of claim 17 wherein said carrier is a pharmaceutically or cosmetically acceptable vehicle.

19. The composition of claim 17 wherein said compound is present in an amount of about 0.001 wt. % to about 50.0 wt. % of the composition.

20. The composition of claim 17 wherein said compound is present in an amount of about 0.005 wt. % to about 10.0 wt. % of composition.

21. The composition of claim 18 wherein said vehicle is selected from the group consisting of lotion, tincture, cream, emulsion, gel and ointment.

22. The composition of claim 17 wherein said composition is a topical composition.

23. A method for treating or retarding lipid peroxidation-medicated skin aging or treating a lipid peroxidation-medicated skin disorder in a patient which comprises topically administrating to skin of a patient in need thereof a composition comprising a lipid peroxidation inhibiting amount of a compound of the formula:

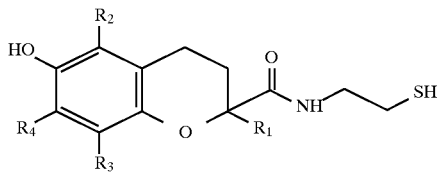

or a pharmaceutically or cosmetically acceptable salt thereof wherein $R_1$ is methyl and $R_2$, $R_3$, $R_4$ are the same or different and are independently selected from H, OH, lower alkoxy, halogen, $NO_2$, $NH_2$ or $N(R_5)_2$, wherein $R_5$ is lower alkyl; and a carrier.

24. The method of claim 23 wherein said skin disorder is selected from the group consisting of dry skin, severe dry skin, terosis, dandruff, keratoses, psoriasis, eczema, erythema, age spots, lentigines, melasmas, wrinkles, blemished skin, hyperpigmented skin, hyperkertatic skin and inflammatory dermatoses.

25. The method of claim 23 wherein said skin aging is age-related skin changes.

26. The method of claim 23 wherein said compound is present in an amount of about 0.001 wt. % to about 50.0 wt. % of the composition.

27. The method of claim 23 wherein said compound is present in an amount of about 0.005 wt. % to about 10.0 wt. % of the composition.

28. The method of claim 23 wherein said carrier is selected from the group consisting of lotion, tincture, cream, emulsion, gel and ointment.

* * * * *